United States Patent
Zhang et al.

(10) Patent No.: US 11,241,524 B2
(45) Date of Patent: Feb. 8, 2022

(54) DIALYSIS MACHINE AND METHOD OF CORRECTING THE BLOOD FLOW VALUE

(71) Applicant: FRESENIUS MEDICAL CARE DEUTSCHLAND GMBH, Bad Homburg (DE)

(72) Inventors: Wei Zhang, Niederwerrn (DE); Christoph Bardorz, Rottendorf (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 573 days.

(21) Appl. No.: 16/318,617

(22) PCT Filed: Jul. 19, 2017

(86) PCT No.: PCT/EP2017/000880
§ 371 (c)(1),
(2) Date: Jan. 17, 2019

(87) PCT Pub. No.: WO2018/015017
PCT Pub. Date: Jan. 25, 2018

(65) Prior Publication Data
US 2019/0282748 A1    Sep. 19, 2019

(30) Foreign Application Priority Data
Jul. 19, 2016 (DE) .................... 10 2016 008 821.4

(51) Int. Cl.
*A61M 1/36* (2006.01)
*A61M 1/16* (2006.01)

(52) U.S. Cl.
CPC ........ *A61M 1/3639* (2013.01); *A61M 1/3609* (2014.02); *A61M 1/1601* (2014.02);
(Continued)

(58) Field of Classification Search
CPC .............. A61M 1/3639; A61M 1/3609; A61M 1/1601; A61M 2205/14;
(Continued)

(56) References Cited

U.S. PATENT DOCUMENTS

2002/0151804 A1   10/2002   O'Mahony et al.
2013/0072846 A1    3/2013   Heide et al.
2015/0335809 A1   11/2015   Stuva et al.

FOREIGN PATENT DOCUMENTS

WO    WO 02/004044    1/2002

OTHER PUBLICATIONS

Gillum et al. Blood Pump Speed vs. Actual or "Compensated" Blood Flow Rate. Nephrology Nursing Journal, 2007, S491-525.
(Continued)

*Primary Examiner* — Leslie R Deak
(74) *Attorney, Agent, or Firm* — Jacobson Holman PLLC

(57) ABSTRACT

The invention relates to a dialysis machine having an extracorporeal blood circuit in which a dialyzer, a blood pump, and an arterial pressure sensor are arranged, wherein the dialysis machine furthermore has a compensation device by means of which the set value for the blood flow through the extracorporeal circuit can be corrected to a compensated value using the arterial blood pressure; wherein the dialysis machine furthermore has recognition means which are configured to recognize whether the arterial pressure sensor is connected to the extracorporeal blood circuit or not; and wherein the dialysis machine has an estimator unit which is configured to estimate a value for the arterial blood pressure if it is recognized by the recognition means that the arterial pressure sensor is not connected to the extracorporeal blood circuit.

15 Claims, 1 Drawing Sheet

(52) U.S. Cl.
CPC ..... *A61M 2205/14* (2013.01); *A61M 2205/16* (2013.01); *A61M 2205/3331* (2013.01); *A61M 2230/207* (2013.01); *A61M 2230/30* (2013.01)

(58) Field of Classification Search
CPC .... A61M 2205/3331; A61M 2230/207; A61M 2230/30; A61M 1/3656
See application file for complete search history.

(56) References Cited

OTHER PUBLICATIONS

Mehta et al., Correction of Discrepancy Between Prescribed and Actual Blood Flow Rates in Chronic Hemodialysis Patients with Use of Larger Gauge Needles. American Journal of Kidney Diseases, vol. 39, No. 6 Jun. 2002, pp. 1231-1235.

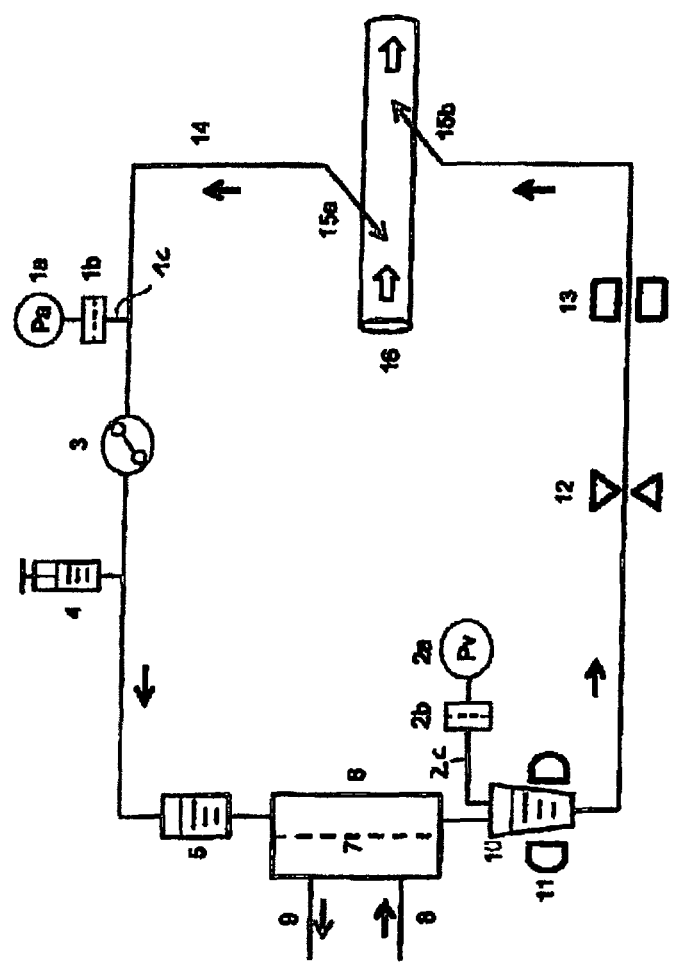

DIALYSIS MACHINE AND METHOD OF CORRECTING THE BLOOD FLOW VALUE

The present invention relates to a dialysis machine having an extracorporeal blood circuit in which a dialyzer, an arterial pressure sensor and a blood pump are arranged, wherein the dialysis machine furthermore has a compensation device by means of which the set value for the blood flow can be corrected to a compensated value by the extracorporeal blood circuit using the arterial blood pressure.

Dialysis machines are known from the prior art which have an arterial pressure sensor in the extracorporeal circuit between the arterial needle and the blood pump. Said arterial pressure sensor serves the detection of the arterial pressure during a dialysis treatment. The pressure sensor is connected to an arterial line of the extracorporeal blood circuit via a pressure return line. The pressure return line typically has a transducer protector ("TP" in the following) which protects the pressure sensor from contact with the patient's blood. This is typically achieved by a hydrophobic membrane in the TP.

The TP thus serves to separate the blood side from the machine side and prevents the contamination of the machine by blood which flows through the extracorporeal circuit. This may otherwise result in cross-contaminations between patients.

The TP is typically located in a pressure return line, i.e. e.g. in a hose piece which connects the extracorporeal blood circuit, in particular its arterial section, to the arterial pressure sensor. The TP typically includes a hydrophobic membrane which keeps the blood away from the pressure sensor.

Known dialysis machines furthermore have a compensation device which corrects the value set for the blood flow through the extracorporeal circuit by a user of the dialysis machine using the value of the arterial blood pressure, wherein the corrected value is used as the basis of the treatment. This correction is necessary since the calculated effective blood flow may possibly not correspond to the actual set pumping rate due to an ovalized hose cross-section upstream of the blood pump.

The arterial pressure in the blood is thus required to provide a value for a compensated blood flow. It is in this respect known from the prior art to determine the compensated, i.e. corrected, blood flow $Q_b$ from the set blood flow $Q_{b,set}$ in accordance with the following relationship.

$$Q_b = Q_{b,set}(\alpha + \beta * P_a) \qquad (1)$$

where: $\alpha=1.0$ and $\beta=0.00057$; Q in [ml/min], $P_a$ in [mmHg]

If the arterial pressure return line is not connected, the atmospheric pressure ($P_a=0$ mmHg) is always measured at the arterial pressure sensor. In accordance with equation (1), this means that the displayed blood flow $Q_b$ is equal to the set blood flow $Q_{b,set}$, that is no correction takes place. This can in turn have the result that the displayed value for $Q_b$ exceeds the value $Q_{b,set}$ set by the user by more than 11%. This has the consequence that the medical prescription or the accumulated purified blood volume for a dialysis treatment is not reached since the real effective blood flow rate is smaller than that set by the user.

It is known from practice that treatments are carried out without a connected pressure return line and thus without a connected pressure sensor, which represents a misuse of the dialysis machine. A realistic indication of the actual blood flow should nevertheless be possible for this case.

It is known from WO 02/04044 A1 to measure the amplitude of the periodic fluctuations of the pressure which are due to revolutions of the blood pump in the venous blood line and to compare it to a threshold value for the detection of arterial inflow problems during an extracorporeal blood treatment. A conclusion of inflow problems is made on an exceeding of the threshold value. In a dialysis apparatus which has a dialysis fluid system, the pressure in the dialysis fluid system can also be monitored instead of the pressure in the venous blood line. No arterial blood pressure measurement has to take place. US 2013/072846 A1 describes a method of determining the blood pressure downstream of the blood pump by measuring the blood pressure downstream of the blood pump.

It is the underlying object of the present invention to further develop a dialysis machine of the initially named kind such that the display of a realistic value for the blood flow is possible even with a non-connected arterial pressure sensor, in particular with a non-connected arterial pressure return line.

This object is satisfied by a dialysis machine having the features of claim 1.

Provision is accordingly made that the dialysis machine furthermore has recognition means which are configured to recognize whether the arterial pressure sensor is connected to the extracorporeal blood circuit or not and that the dialysis machine has an estimator unit which is configured to estimate a value for the arterial blood pressure (Pa) if it is recognized by the recognition means that the arterial pressure sensor is not connected to the extracorporeal blood circuit, which can, for example be due to the fact that the arterial pressure return line has not been used.

The present invention is thus based on the idea of also being able to provide a compensation or correction of the blood flow set in the extracorporeal circuit which is as reliable as possible on the lack of a connection of the pressure sensor to the extracorporeal blood circuit. In this respect, the recognition means have the object of determining whether the arterial pressure sensor is connected or not and the estimator means have the object of providing a replacement value for the arterial blood pressure (not measured) in the extracorporeal circuit for the case that no arterial pressure sensor is connected.

A "connected pressure sensor" is to be understood such that the pressure sensor is connected to the extracorporeal circuit such that it is able to measure the pressure in the extracorporeal circuit.

The non-connection of a pressure sensor can be due to the lack of the pressure return line, i.e. of the hose piece or line piece, which connects the extracorporeal circuit to the pressure sensor and in which the TP is typically located.

The latter can be used to carry out the compensation of the blood flow. The compensated, i.e. corrected, value for the blood flow can then be used as the basis for the treatment, can be displayed, etc.

Provision is made in a conceivable configuration that said compensation device is configured to determine the value for the compensated blood flow in accordance with the above equation (1). When this equation is used, it is not the measured arterial blood pressure which is used for $P_a$, but rather the estimated arterial blood pressure.

The estimator unit can be configured to estimate the arterial blood pressure to a constant value, preferably to the value of $P_a=-200$ mmHg. Irrespective of the set blood flow, a value for $Q_b$ can e.g. be determined in accordance with equation (1) with a constant value for $P_a$. The value of $-200$ mmHg indicated by way of example approximately corresponds to the pressure value which results with a blood flow of $Q_{b,set}=300$ ml/min during a normal dialysis treatment.

In a further embodiment of the invention, the estimator unit is configured to estimate the arterial blood pressure in dependence on the blood flow $Q_{b,set}$ set by the user, wherein a memory or another calculation means is provided in which a relationship is stored between the arterial blood pressure $P_a$ and the blood flow $Q_{b,set}$ set by the user. A curve or a table for the relationship $P_a=f(Q_{b,set})$ is conceivable, for example. The value for $P_a$ can then be determined from $Q_{b,set}$ on the basis of these values which can be stored in software and finally the blood flow can e.g. be calculated in accordance with equation (1).

The estimator unit can furthermore be configured such that further parameters play a role in the named relationship between the set blood flow and the arterial blood pressure. A property of the cannula used, such as its outer diameter and/or the hematocrit value HKT of the blood, can be considered, for example.

With a given arterial blood hose, the relationship between the estimated arterial blood pressure and the set blood flow can thus still be influenced by the dialysis cannula and/or by the hematocrit value of the blood. In principle, a family of curves or tables can be determined experimentally for the function $P_a=f(Q_{b,set})$ in dependence on the dialysis cannula and on the hematocrit and can be stored in the software. The type of dialysis cannula and the hematocrit value can be fixed by a user specification via a user interface prior to a dialysis treatment. It is also conceivable that the hematocrit value is measured during the dialysis by a dialysis machine and the measured value is then used accordingly.

Typical dialysis cannulas are:
16 G with a 1.6 mm outer diameter
17 G with a 1.5 mm outer diameter
15 G with a 1.8 mm outer diameter.

Typical values for the hematocrit value lie in the range between 27 and 42%.

It is advantageous for an implementation of this embodiment of the invention to determine the relationship between the estimated arterial blood pressure and the set blood flow with a typical dialysis cannula, e.g. with a 16 G needle, and with a typical hematocrit value, e.g. 35%, and then to store it in the software.

Provision is made in a further embodiment of the invention that the estimator unit is configured to estimate the arterial blood pressure in dependence on the measured venous blood pressure in the extracorporeal blood circuit.

This embodiment of the invention will be explained in more detail with reference to the single FIGURE which represents an extracorporeal blood circuit of a hemodialysis machine in accordance with the invention.

In this respect, the reference numeral 16 designates the blood port which can be configured as a fistula or as a shunt and reference numerals 15a and 15b designate the arterial needle and the venous needle.

The blood moves from the arterial needle 15a through the blood hose 14 over the arterial pressure return line 1c to the arterial TP having the reference numeral 1b to which the arterial pressure sensor 1a is connected for measuring the arterial pressure $P_a$. The blood pump 3 is located downstream thereof and the heparin pump 4 is located downstream of the blood pump. The arterial bubble trap 5 is located between the heparin pump 4 and the dialyzer.

The dashed line in 1b represents the transition from the hose system to the dialysis machine. The pressure return line is connected to the pressure sensor there, e.g. by a Luer lock connection.

The dialyzer is designated by the reference numeral 6 and is divided by a semipermeable membrane 7, preferably by a hollow fiber bundle, into a dialyzate chamber and a blood chamber, wherein the dialyzate infeed 8 and the dialyzate outfeed 9 are connected to the dialyzate chamber.

The venous drip chamber 10 having a level detector 11 is located downstream of the dialyzer 6. The venous pressure return line 2c, which is in communication with the venous pressure sensor having the reference numeral 2a for measuring the venous blood pressure $P_v$ is connected to the venous drip chamber 10. The venous TP having the reference numeral 2b is introduced into the venous pressure return line.

A venous clamp 12, by means of which the blood hose can be blocked and the optical detector 13 for recognizing air bubbles in the blood are located downstream of the venous drip chamber 10.

The blood moves back into the fistula or into the shunt 16 via the venous needle 15b.

It will now be shown in the following how a conclusion can be drawn on the arterial blood pressure $P_a$ with reference to the venous blood pressure $P_v$ which can e.g. be measured in or at the venous drip chamber 10.

$Q_b=(P_{f,a}-P_a)/R_a$ applies to the arterial side of the extracorporeal blood circuit analogously to Ohm's law. If this equation is resolved for $P_a$, $$P_a=P_{f,a}-Q_b*R_a \quad (2')$$

results. $Q_b-Q_{UF}=(P_v-P_{f,v})/R_v$ results at the venous side of the extracorporeal blood circuit.

If this equation is resolved for the venous pressure:

$$P_v=(Q_b-Q_{UF})*R_v+P_{f,v} \quad (3')$$

results. If equations (2') and (3') are added:

$$P_a+P_v=Q_b*(R_v-R_a)+(P_{f,a}+P_{f,v})-Q_{UF}*R_v \quad (4')$$

results. Within the framework of the present invention: $P_f$ is the fistula pressure, $P_{f,a}$ is the fistula pressure at the point of the arterial dialysis needle, $P_{f,v}$ is the fistula pressure at the point of the venous dialysis needle, $P_a$ is the arterial pressure before the blood pump, $P_v$ is the venous pressure at the venous drip chamber, $P_{v,0}$ is the measured venous pressure on a stop of the blood pump and with an open venous clamp, $Q_{b,set}$ is the set blood flow, $Q_b$ is the compensated blood flow, $Q_{UF}$ is the ultrafiltration rate, $R_a$ is the flow resistance between the arterial pressure return line 1c and the tip of the arterial needle, $R_v$ is the flow resistance between the venous drip chamber and the tip of the venous needle, and MAP is the mean measured arterial blood pressure of the dialysis patient.

The length of the arterial hose section between the arterial pressure return line and the arterial needle connector is almost identical to the length of the venous hose section between the venous drip chamber and the venous needle connector. This length can amount to approximately 190 cm, for example. When taking account of the fact that arterial and venous needles of the same type are used in a routine analysis, e.g. 16 G, the flow resistances of the above-named hose sections are also almost identical, that is $R_a=R_v$ applies in equation (4'). It results from this:

$$P_a=(P_{f,a}+P_{f,v})-Q_{UF}*R_v-P_v \quad (5')$$

The ultrafiltration rate $Q_{UF}$ is relatively small in the dialysis. If this value is neglected or if $P_a$ is measured with a switched-off ultrafiltration, the following relationship results from equation (5'):

$$P_a=(P_{f,a}+P_{f,v})-P_v \quad (6')$$

The pressures in the shunt or in the fistula can be estimated as follows:

It applies to the case of the fistula:

$$P_{f,a}=0.20*MAP$$

$$P_{f,v}=0.15*MAP$$

$$P_{f,a}=1.33*P_{f,v}$$

The following relationships apply to the shunt:

$$P_{f,a}=0.55*MAP$$

$$P_{f,v}=0.35*MAP$$

$$P_{f,a}=1.57*P_{f,v}$$

It results from this from equation (6') in the fistula case $$P_a=0.35*MAP-P_v \quad (7')$$

and $$P_a=2.33*P_{f,v}-P_v \quad (8')$$

It results from equation (6') in the shunt case $$P_a=0.90*MAP-P_v \quad (9')$$

and $$P_a=2.57*P_{f,v}-P_v \quad (10')$$

It is obligatory in hemodialysis to measure the blood pressure of a patient. The mean arterial blood pressure MAP in equations (7') and (9') is therefore known. This MAP value can either be determined automatically by a blood pressure monitor (BPM) integrated into the dialysis machine or can be input manually via the user interface. In these cases, the sought value $P_a$ can be determined with a measured $P_v$ in accordance with equation (7') or in accordance with equation (9').

As can be seen from the equations (8') and (10'), the value $P_{f,v}$ is required for determining $P_a$ in these cases and $P_{f,v}$ can be determined in a further preferred embodiment by the relationship $P_{f,v}=P_{v0}+14.72$.

This relationship results as follows:

After the connection of the patient to the extracorporeal blood circuit, the blood pump is started and the patient blood is conveyed into the extracorporeal blood circuit. As soon as the optical detector recognizes the blood at the venous drip chamber, the blood pump is stopped and the venous clamp 12 is closed. The user is subsequently asked whether the dialysis treatment should be started. If the venous clamp is briefly opened in this case, the venous pressure is measured as $P_{v0}$.

While taking account of the hydrostatic pressure between the fistula port at the patient's arm and the venous pressure return line 2c, the value for $P_{f,v}$ is calculated in accordance with $$P_{f,v}=P_{v0}+r*g*H \quad (11')$$

Here, r is the water density and amounts to 1000 kg/m³, H is the height difference between the fistula port and the venous pressure return line 2c, e.g. 20 cm, and g is the acceleration due to gravity (9.81 m/s²). It results for the fistula from equations (8'), (10') and (11')

$$P_a=2.33*(P_{v0}+r*g*H)-P_v \quad (12')$$

and for the shunt $$Pa=2.57*(P_{v0}+r*g*H)-P_v \quad (13')$$

With a height difference of 0.2 m, it results therefrom:

$$r*g*H=1000*9.81*0.2=14.72 mmHg.$$

If this value is used in equation (11'), the named relationship results, that is $$P_{f,v}=P_{v0}+14.72 [mmHg] \quad (14')$$

With knowledge of this value and of the venous blood pressure, the value $P_a$ can be determined from equations (8') and (10').

Provision is made in a further embodiment of the invention that the recognition means are configured to determine the signal detected by means of the arterial pressure sensor, to carry out an ongoing mean value formation and variance calculation over a specific time period, e.g. over a minute, and to draw a conclusion on the presence or absence of a connected arterial pressure sensor with reference to the evaluation of the mean value and the variance value. The lack of this connection can be due to the fact, for example, that the arterial pressure return line (having the TP located therein) is not inserted so that the arterial pressure sensor cannot measure the pressure in the extracorporeal blood circuit.

Provision is made in an alternative or additionally usable embodiment that the recognition means are configured to determine the pressure signal detected by means of the arterial pressure sensor, to start and to stop the blood pump while the blood hose system is filled, to determine and to evaluate the signal change of the arterial blood pressure and, based on this, to draw a conclusion on the absence or presence of the arterial pressure return line or of the connection of the arterial pressure sensor.

If no connected pressure sensor is recognized, the blood flow compensation is carried out with the aid of the above-described method, wherein equation (1) is preferably used, where a value estimated in accordance with the invention is used for $P_a$.

Otherwise, the measured value is used for $P_a$.

The present invention furthermore relates to a method of correcting a set value for the blood flow using the arterial blood pressure to a compensated value in a dialysis machine having an extracorporeal blood circuit in which a dialyzer, a blood pump and an arterial pressure sensor are arranged, with it being detected whether the pressure sensor is connected to the extracorporeal circuit or not and with a value for the arterial blood pressure being estimated if it is found that this is not the case. In this respect, the value for the compensated blood flow can be determined in accordance with the above equation (1).

The arterial blood pressure can be estimated to a constant value such as to the value −200 mmHg. It is also possible to estimate the arterial blood pressure in dependence on the blood flow set by the user, with a corresponding relationship between the arterial blood pressure and the set blood flow being stored by software or in a memory or by a computation unit. In this respect, further parameters can play a role, in particular the kind of dialysis cannula used and in particular its outer diameter and/or the measured or entered hematocrit value of the blood.

It is also conceivable, as stated above, that the arterial blood pressure is estimated in dependence on the venous blood pressure in the extracorporeal circuit.

It is conceivable in this respect that the following relationships are used:

$$P_a=0.35*MAP-P_v,$$

$$P_a=2.33*P_{f,v}-P_v$$

or $$P_a=0.90*MAP-P_v,$$

$$P_a=2.57*P_{f,v}-P_v$$

We refer to the above statements with respect to the derivation of these relationships. Provision is made in a further embodiment of the method that the value $P_{f,v}$ is calculated after blood has been introduced into the extracorporeal circuit up to the venous pressure sensor, that the venous pressure clamp is then opened, and the venous blood pressure $P_{v0}$ is then measured with an idling blood pump. The value of $P_{f,v}$ then results from the relationship $P_{f,v}=P_{v0}+14.72$. We likewise refer to the above statements for the determination of this equation.

Provision is made in a further embodiment of the method that the pressure signal detected by the arterial pressure sensor is determined for the recognition of the presence or absence of the connection of the arterial pressure sensor and a check is made with reference to an ongoing mean value formation and variance calculation over a certain time period whether the pressure sensor is connected or not. It is also conceivable to determine the pressure signal detected by the arterial pressure sensor while the blood pump is being started and stopped again. The pressure signal provides conclusions on the presence or absence of the connection of the arterial pressure sensor or of the arterial pressure return line.

It is generally conceivable that the recognition whether the pressure sensor is connected is based on the fact that the pressure sensor does not measure any pressure fluctuations although the blood pump is running or that a pressure pulse is output by the blood pump which is not measured at the pressure sensor.

Further details and advantages of the invention will be explained in more detail with reference to an embodiment described in the drawing and in the following.

The only FIGURE shows an extracorporeal blood circuit which is connected via a venous needle and via an arterial needle to a fistula or to a shunt of the patient.

An input is first made via a user interface of the dialysis machine which is not shown in the drawing and in which the extracorporeal blood circuit in accordance with the FIGURE is inserted whether the blood port is a fistula or a shunt. The input of the measured MAP, that is of the mean blood pressure of the patient, then takes place.

From the time of the blood recognition by the optical detector 13 onward the values for $P_a$ and $P_v$ are evaluated in segments, e.g. every two minutes, to recognize a non-connected pressure sensor or pressure return line. If it is recognized that both pressure sensors or pressure return lines are connected, that is the arterial and the venous pressure sensors or return lines, the blood flow is compensated in accordance with equation (1), where the measured arterial blood pressure is used for $P_a$.

If it is found that neither of the pressure sensors, that is neither the venous pressure sensor nor the arterial pressure sensor, is connected, a warning is output which prompts the user to connect both pressure sensors. If it is found that the venous pressure sensor is connected, but not the arterial pressure sensor, a warning is output which prompts the user also to connect the arterial pressure sensor. If this is not done, the method continues as follows.

The venous pressure of the blood in the extracorporeal circuit, that is $P_v$, is measured with a running blood pump during the normal dialysis treatment. The formation of an ongoing mean value of $P_v$ then takes place.

In accordance with equation (7') or in accordance with equation (9'), the calculation, that is the estimation of $P_a$, takes place for the fistula or for the shunt. Based on these values, the value for the compensated blood flow, that is $Q_b$, can then be determined by means of equation (1).

It is conceivable in this respect that this value is restricted to the range $$0.85Q_{b,set} \leq Q_b \leq Q_{b,set}$$

The compensation process is preferably only carried out for the active dialysis phase, that is when blood is recognized in the system, the blood pump is running and the dialysis is alarm-free. A compensation in the phase of preparation and of reinfusion is admittedly conceivable, but not necessary in principle.

It is finally pointed out that the term "one" used within the framework of the invention covers a single one of the respective elements, but also a plurality of these elements, i.e. is not necessarily to be equated as "one/one single".

The invention claimed is:

1. A dialysis machine having an extracorporeal blood circuit (1) in which a dialyzer (6), a blood pump (3) and an arterial pressure sensor (1a) are arranged, wherein the dialysis machine furthermore has a compensation device by means of which the value set for the blood flow ($Q_{b,set}$) can be corrected to a compensated value ($Q_b$) by the extracorporeal circuit (1) using the arterial blood pressure ($P_a$),
    characterized in that the dialysis machine furthermore has detection means which are configured to recognize whether the arterial pressure sensor (1a) is connected to the extracorporeal blood circuit (1) or not; and in that the dialysis machine has an estimator unit which is configured to estimate a value for the arterial blood pressure ($P_a$) if it is recognized by the recognition means that the arterial pressure sensor (1a) is not connected to the extracorporeal blood circuit (1).

2. A dialysis machine in accordance with claim 1, characterized in that the dialysis machine is configured such that a pressure return line (1c) can be connected which connects the arterial pressure sensor (1a) to the extracorporeal blood circuit (1) in the connected state; and in that the recognition means are configured to recognize whether the pressure return line (1c) is connected or not.

3. A dialysis machine in accordance with claim 1, characterized in that the compensation device is configured to determine the value for the compensated blood flow ($Q_b$) in [ml/min] in accordance with equation (1):

$$Q_b = Q_{b,set}(\alpha + \beta * P_a) \quad (1),$$

where $\alpha$ adopts the value 1.0 and $\beta$ adopts the value 0.00057 and $P_a$ is used as a value in [mmHg].

4. A dialysis machine in accordance with claim 1, characterized in that the estimator unit is configured to estimate the arterial blood pressure ($P_a$) to a constant value, preferably to the value –200 mmHg; and/or in that the estimator unit is configured to estimate the arterial blood pressure ($P_a$) in dependence on the blood flow ($Q_{b,set}$) set by the user, with a memory or a calculation unit being provided in which a relationship is stored between the arterial blood pressure ($P_a$) and the blood flow ($Q_{b,set}$) set by the user, with provision preferably being made that the estimator unit is configured such that a property of the used dialysis cannula and/or the hematocrit value (HKT) of the blood is taken into the named relationship as a further parameter.

5. A dialysis machine in accordance with claim 1, characterized in that the estimator unit is configured to estimate the arterial blood pressure ($P_a$) in dependence on the venous blood pressure ($P_v$) in the extracorporeal blood circuit, with provision preferably being made that the estimator unit is configured to determine the arterial blood pressure ($P_a$) in [mmHg] in accordance with one of the relationships ($P_v$: venous blood pressure in the extracorporeal circuit; MAP: mean blood pressure; $P_{f,v}$, fistula pressure/shunt pressure at the point of the venous dialysis needle)

$$P_a = 0.35 * MAP - P_v \quad (2)$$

$$P_a = 2.33 * P_{f,v} - P_v \quad (3)$$

$$P_a = 0.90 * MAP - P_v \quad (4)$$

$$P_a = 2.57 * P_{f,v} - P_v \quad (5),$$

with equations (2) and (3) being applied for the use of a fistula and equations (4) and (5) being applied for the use of a shunt.

6. A dialysis machine in accordance with claim 5, characterized in that the dialysis machine has a computation unit for determining $P_{f,v}$; and in that this computation unit is configured to open a venous pressure clamp (12) after the introduction of blood into the extracorporeal circuit up to the venous pressure sensor and then to measure the venous blood pressure ($P_{v0}$) with an idling blood pump; and in that the computation unit is configured to determine the value for $P_{f,v}$ in [mmHg] as follows:

$$P_{f,v} = P_{v0} + 14.72 \quad (6).$$

7. A dialysis machine in accordance with claim 1, characterized in that the recognition means are configured to determine the pressure signal detected by means of the arterial pressure sensor (1a), to carry out an ongoing mean value formation and variance calculation over a specific period in time and to draw a conclusion on the presence or absence of the connection of the arterial pressure sensor (1a) to the extracorporeal blood circuit (1) with reference to the evaluation of the mean value and the variance value.

8. A dialysis machine in accordance with claim 1, characterized in that the recognition means are configured to determine the pressure signal detected by means of the arterial pressure sensor (1a), to start the blood pump and to stop it again, to determine the change of the arterial blood pressure ($P_a$) and, based on this, to draw a conclusion on the presence or absence of the connection of the arterial pressure sensor (1a) to the extracorporeal blood circuit (1).

9. A method of correcting a set value for the blood flow ($Q_{b,set}$) using the arterial blood pressure ($P_a$) to a compensated value ($Q_b$) in a dialysis machine having an extracorporeal blood circuit (1) in which a dialyzer (6), a blood pump (3) and an arterial pressure sensor (11) are arranged,
characterized in that a detection is made whether the arterial pressure sensor (11) is connected to the extracorporeal circuit (1) or not; and in that a value is estimated for the arterial blood pressure ($P_a$) if it is found that the arterial pressure sensor (11) is not connected to the extracorporeal circuit (1).

10. A method in accordance with claim 9, characterized in that the value for the compensated blood flow ($Q_b$) is determined in [ml/min] in accordance with equation (1):

$$Q_b = Q_{b,set}(\alpha + \beta * P_a) \quad (1),$$

where $\alpha$ adopts the value 1.0 and $\beta$ adopts the value 0.00057 and $P_a$ is used as a value in [mmHg].

11. A method in accordance with claim 9, characterized in that the arterial blood pressure ($P_a$) is estimated to a constant value, preferably to the value −200 mmHg; and/or in that the arterial blood pressure ($P_a$) is estimated in dependence on the blood flow ($Q_{b,set}$) set by the user, with a relationship between the arterial blood pressure ($P_a$) and the blood flow ($Q_{b,set}$) set by the user being retrievably stored, with provision preferably being made that a property of the dialysis cannula used and/or the hematocrit value (HKT) of the blood is taken into the named relationship as a further parameter.

12. A method in accordance with claim 9, characterized in that the arterial blood pressure ($P_a$) is estimated in dependence on the venous blood pressure ($P_v$) in the extracorporeal circuit, with provision preferably being made that the arterial blood pressure ($P_a$) is determined in [mmHg] in accordance with one of the relationships ($P_v$: venous blood pressure in the extracorporeal circuit; MAP: mean blood pressure; $P_{f,v}$: fistula pressure/shunt pressure at the point of the venous dialysis needle)

$$P_a = 0.35 * MAP - P_v \quad (2)$$

$$P_a = 2.33 * P_{f,v} - P_v \quad (3)$$

$$P_a = 0.90 * MAP - P_v \quad (4)$$

$$P_a = 2.57 * P_{f,v} - P_v \quad (5),$$

with equations (2) and (3) being applied for the use of a fistula and equations (4) and (5) being applied for the use of a shunt.

13. A method in accordance with claim 12, characterized in that $P_{f,v}$ is determined, with a venous pressure clamp (12) being opened after the introduction of blood into the extracorporeal circuit up to the venous pressure sensor and the venous blood pressure ($P_{v0}$) the being measured with an idling blood pump; and in that the value for $P_{f,v}$ is then determined in [mmHg] as follows:

$$P_{f,v} = P_{v0} + 14.72 \quad (6).$$

14. A method in accordance with claim 9, characterized in that, for the recognition of the present or absent connection of the arterial pressure sensor (1a) at the extracorporeal circuit (1), the pressure signal detected by the arterial pressure sensor (1a) is determined, an ongoing mean value formation and variance calculation is carried out over a specific time period, and a conclusion is drawn on the presence or absence of the connection of the arterial pressure sensor (1a) at the extracorporeal circuit (1) with reference to the evaluation of the mean value and the variance value.

15. A method in accordance with claim 9, characterized in that, for recognizing the presence or absence of the arterial pressure sensor (1a) at the extracorporeal circuit (1), the pressure signal detected by the arterial pressure sensor (1a) is determined, the blood pump is started and stopped again, the change of the arterial blood pressure ($P_a$) is determined and, based on this, a conclusion is drawn on the presence or absence of the arterial pressure sensor (1a) at the extracorporeal circuit (1); and/or in that a pressure return line (1c) can be connected which connects the arterial pressure sensor (1a) to the extracorporeal blood circuit (1) in the connected state; and in that the recognition of the presence or absence of the connection of the arterial sensor (1a) at the extracorporeal circuit comprises a recognition being made whether the pressure return line (1*c*) is connected or not.

* * * * *